United States Patent
Constant et al.

(10) Patent No.: US 10,232,089 B2
(45) Date of Patent: Mar. 19, 2019

(54) EMBOLIC DEVICES

(71) Applicant: Terumo Corporation, Tokyo (JP)

(72) Inventors: Michael Constant, Mission Viejo, CA (US); Josh Garretson, San Diego, CA (US); Gregory M. Cruise, Rancho Santa Margarita, CA (US)

(73) Assignee: Terumo Corporation (JP)

( * ) Notice: Subject to any disclaimer, the term of this patent is extended or adjusted under 35 U.S.C. 154(b) by 225 days.

(21) Appl. No.: 15/252,089

(22) Filed: Aug. 30, 2016

(65) Prior Publication Data

US 2016/0367730 A1 Dec. 22, 2016

Related U.S. Application Data

(62) Division of application No. 13/450,287, filed on Apr. 18, 2012, now Pat. No. 9,456,823.
(Continued)

(51) Int. Cl.
| | |
|---|---|
| *A61L 31/04* | (2006.01) |
| *A61L 31/06* | (2006.01) |
| *A61L 31/14* | (2006.01) |
| *A61L 31/18* | (2006.01) |
| *A61B 17/12* | (2006.01) |

(Continued)

(52) U.S. Cl.
CPC ........ *A61L 31/048* (2013.01); *A61B 17/1214* (2013.01); *A61B 17/1215* (2013.01); *A61B 90/39* (2016.02); *A61L 31/06* (2013.01); *A61L 31/14* (2013.01); *A61L 31/145* (2013.01); *A61L 31/18* (2013.01); *C08F 222/385* (2013.01); *A61B 2090/3966* (2016.02); *A61L 2430/36* (2013.01);

(Continued)

(58) Field of Classification Search
CPC ...... A61L 31/048; A61L 31/14; A61L 31/145; C08F 222/385; A61B 17/1214; A61B 17/12145; A61B 17/1215
See application file for complete search history.

(56) References Cited

U.S. PATENT DOCUMENTS

| | | |
|---|---|---|
| 5,447,727 A | 9/1995 | Graham |
| 5,863,551 A | 1/1999 | Woerly |
| 2003/0203991 A1 | 10/2003 | Schottman et al. |
| 2004/0247867 A1 | 12/2004 | Chaouk et al. |

(Continued)

FOREIGN PATENT DOCUMENTS

| | | |
|---|---|---|
| WO | 1991/004732 A1 | 9/1990 |
| WO | 1998/055103 A1 | 12/1998 |

(Continued)

OTHER PUBLICATIONS

Supplementary European Search Report for EP Application No. 15785350 dated Nov. 13, 2017.
(Continued)

*Primary Examiner* — Robert Lynch
(74) *Attorney, Agent, or Firm* — K&L Gates LLP; Louis C. Cullman; Brian J. Novak (57) ABSTRACT

Described herein are apparatus, compositions, systems and associated methods to occlude structures and malformations of the vasculature with radiopaque hydrogel filaments with delayed controlled rates of expansion. Further described is a device for implantation in an animal comprising a difunctional, low molecular weight ethylenically unsaturated shapeable macromer; an ethylenically unsaturated monomer; and a radiopaque element, wherein said device contains no support members. Methods of forming such devices are also disclosed.

20 Claims, 3 Drawing Sheets

Related U.S. Application Data

(60) Provisional application No. 61/476,692, filed on Apr. 18, 2011.

(51) Int. Cl.
*A61B 90/00* (2016.01)
*C08F 222/38* (2006.01)
*A61M 25/00* (2006.01)
*A61M 25/01* (2006.01)

(52) U.S. Cl.
CPC ..... *A61M 25/0097* (2013.01); *A61M 25/0122* (2013.01); *A61M 2025/0042* (2013.01)

(56) References Cited

U.S. PATENT DOCUMENTS

| | | |
|---|---|---|
| 2006/0270750 A1 | 11/2006 | Almen et al. |
| 2011/0027172 A1 | 2/2011 | Wang et al. |
| 2016/0345978 A1 | 12/2016 | Cruise et al. |
| 2016/0361459 A1 | 12/2016 | Baldwin |
| 2017/0007264 A1 | 1/2017 | Cruise et al. |
| 2017/0290593 A1 | 10/2017 | Cruise et al. |
| 2018/0110527 A1 | 4/2018 | Cruise et al. |

FOREIGN PATENT DOCUMENTS

| | | |
|---|---|---|
| WO | 2012/039602 A1 | 3/2012 |
| WO | 2016/201250 A1 | 12/2016 |

OTHER PUBLICATIONS

U.S. Appl. No. 15/635,046, filed Jun. 27, 2017.
U.S. Appl. No. 15/847,745, filed Dec. 19, 2017.

EMBOLIC DEVICES

CROSS REFERENCE TO RELATED APPLICATIONS

This application is a divisional of U.S. patent application Ser. No. 13/450,287, filed Apr. 18, 2012, which claims the benefit of U.S. provisional patent application No. 61/476,692, filed Apr. 18, 2011, the entire disclosures each of which are incorporated herein by reference.

FIELD OF THE INVENTION

The present invention relates generally to implantable hydrogel filaments and medical treatment methods using the hydrogel filaments, wherein the filaments can be visualized using medically relevant imaging techniques.

BACKGROUND

Despite the number of vascular coil devices available, there exists a clinical need for polymer filament devices that can be deployed using standard microcatheters and catheters to treat sites in the peripheral vasculature. Of particular clinical need is a polymer filament device that can be deployed using standard medical techniques through standard microcatheters and catheters to treat sites in the neuro and peripheral vasculature and can be compatible with various medical imaging techniques such as computed tomography imaging.

SUMMARY

Described herein generally are expansile hydrogel filaments, methods of forming those filaments, and medical treatment methods using the hydrogel filaments. The hydrogel filaments possess enough structural strength not to require metallic support members. The filaments can also be opacified in order to visualize the filaments using medically relevant imaging techniques.

In one embodiment, described are expansile devices for implantation comprising a polymeric filament having at least one difunctional, low molecular weight, ethylenically unsaturated, shapeable macromer; at least one ethylenically unsaturated monomer; and at least one visualization element, wherein the expansile device includes no metal support members. In some embodiments, the expansile devices further comprise a multifunctional, ethylenically unsaturated cross-linker.

In other embodiments, the expansile devices reduce beam hardening artifacts when imaged using computed tomography. The at least one visualization element can be selected from soluble or insoluble opacification compounds, metallic powders, gadolinium, iodine, barium sulfate, superparamagnetic iron oxide particles, or a combination thereof. In another embodiment, the at least one visualization element is barium sulfate.

The expansile devices generally can have diameters of less than about 0.05 inches, 0.04 inches, or 0.031 inches. The expansile devices can also be biostable or biodegradable.

In another embodiment, the at least one ethylenically unsaturated monomer is pH sensitive. In still another embodiment, the at least one difunctional, low molecular weight, ethylenically unsaturated, shapeable macromer is poly (ethylene glycol) 10,000.

Also described herein are methods of forming an environmentally responsive hydrogel comprising: a. preparing a polymerization solution comprising at least one difunctional, low molecular weight, ethylenically unsaturated, shapeable macromer; at least one ethylenically unsaturated monomer; and at least one visualization element in a solvent; b. polymerizing the polymerization solution to create a polymerized hydrogel; and c. treating said polymerized hydrogel in a non-physiological pH for a predetermined amount of time thereby creating an environmentally responsive hydrogel. In another embodiment, step b further comprises polymerizing the polymerization in a tube thereby creating a polymerized hydrogel filament.

In some embodiments, the non-physiological pH is acidic in others it is basic. The solvent can be selected from isopropanol, ethanol, water, dichloromethane, and acetone. The at least one difunctional, low molecular weight, ethylenically unsaturated, shapeable macromer can be poly(ethylene glycol), and in some embodiments have molecular weight of about 5,000 g/mole to about 15,000 g/mole.

In other embodiments, the at least one ethylenically unsaturated monomer is a pH sensitive monomer selected from acrylic acid, methacrylic acid, amino methacrylate, or amino methacrylamide. The polymerization solution can further comprise a cross-linker and that cross-linker can be cross-linker is N,N'-methylenebisacrylamide.

BRIEF DESCRIPTION OF THE DRAWINGS

FIGS. 6A-E illustrate hydrogel filaments according to an embodiment of the present description including barium sulfate.

DETAILED DESCRIPTION

Described herein generally are expansile hydrogel filaments and medical treatment methods using the hydrogel filaments. Methods of forming the hydrogel filaments are also described herein, including methods of making the hydrogel filaments environmentally responsive and expandable at a predetermined rate for a predetermined amount of time. Generally, the hydrogel filaments possess enough structural column strength so as to not require metallic support members. The filaments can also be opacified in order to visualize the filaments using medically relevant imaging techniques.

The hydrogel filaments and associated methods are for occluding structures and malformations resulting from one or more cerebral and/or peripheral vascular diseases. Hydrogel filaments have delayed controlled rates of expansion. These controlled rates of expansion give surgeons a sufficient amount of time to deliver the hydrogel through a microcatheter or catheter filled with blood or saline at physiological pH without the need to rush as a result of immediate filament expansion. Further, the hydrogel filaments include one or more visualization agents, for example, radiopaque elements or fillers.

Generally, the hydrogel filaments can be deployed within the vasculature using standard practices and microcatheters/catheters to occlude blood flow. The polymer filaments are prepared by polymerizing a solution of monomers, macromers, and optionally, cross-linkers. For fluoroscopic and computed tomography visibility, the filaments can be opacified with barium sulfate or metallic powders. For magnetic resonance imaging, the filaments can be opacified with gadolinium or superparamagnetic iron oxide particles.

As used herein, the term "macromer" refers to a large molecule containing at least one active polymerization site or binding site. Macromers have a larger molecular weight than monomers. For example, an acrylamide monomer has a molecular weight of about 71.08 grams/mole whereas a poly(ethylene glycol) di-acrylamide macromer may have a molecular weight of about 1,000 grams/mole or greater. Preferred macromers are non-ionic, i.e. they are uncharged at all pHs and shapeable.

As used herein, the term "environmentally responsive" refers to a material (e.g., a hydrogel) that is sensitive to changes in environment including but not limited to pH, temperature, and pressure. Many of the expansile materials described herein are environmentally responsive at physiological conditions.

As used herein, the term "non-resorbable" refers to a material (e.g., a hydrogel) that cannot be readily and/or substantially degraded and/or absorbed by bodily tissues.

As used herein, the term "unexpanded" refers to the state at which a hydrogel is substantially not hydrated and, therefore, not expanded. In some embodiments described herein, a hydrogel filament is generally unexpanded prior to implantation into a patient.

As used herein, the term "ethylenically unsaturated" refers to a chemical entity (e.g., a macromer, monomer or polymer) containing at least one carbon-carbon double bond.

The hydrogel filaments described herein have no metal support members to aid in supporting the filaments before, during and after implantation. The filaments are generally delivered through a catheter or microcatheter using a liquid flush (e.g. saline). The hydrogel filaments have sufficient column strength to alleviate the need for metal support member, yet soft and flexible enough to navigate through vasculature. However, unlike filaments in the art, the hydrogel filaments described herein do not have sufficient column strength to be advanced out of a catheter device by pushing with a metal wire. Here, as described above, a liquid flush, in some cases a pressurized liquid flush, can be used to advance the hydrogel filament through and out of a catheter or microcatheter.

The filaments described herein are formed from polymerization solutions comprising such components as one or more solvent(s), one or more macromer(s), one or more monomer(s), one or more cross-linker(s), one or more visualization agent(s), and one or more initiator(s). Some components are optional.

The solvent's function is complete dissolution of all macromers, monomers, cross-linkers, initiators, and soluble visualization agents needed to form a particular filament. In some embodiments, the visualization agent or agents do not dissolve in the solvent. If a liquid monomer (e.g. 2-hydroxyethyl methacrylate) is used, a solvent may not be necessary. The solvent, if necessary, is selected based on the solubility of the components of the polymerization solution. Preferred solvents are isopropanol, ethanol, water, dichloromethane, and acetone. However, any number of solvents can be utilized and a skilled artisan can match a solvent to a particular polymer system.

Solvent concentrations range from about 20% w/w to about 80% w/w of the polymerization solution. More preferably, the solvent ranges from about 40% w/w to about 60% w/w or about 30% w/w to about 50% w/w. In one embodiment, the solvent makes up about 40% w/w of the polymerization solution.

The polymerization solutions include at least one macromer. The macromer can be of low molecular weight, shapeable, multifunction (e.g. difunctional), ethylenically unsaturated or a combination thereof. At least one of the macromer's roles is to impart the desired mechanical properties to the hydrogel filaments as well as provide structural framework for the hydrogel. In general, any polymer can function as a macromer; however, polymers with solubility in solvents and functional groups amenable to modifications are preferred. Polyethers, due to their solubility in a variety of solvents, their availability in a variety of forms, and their available hydroxyl groups, are preferred macromers. While poly(ethylene glycol), poly(propylene glycol), ethyoxylated trimethylol propane, and poly(tetramethylene oxide) are all polyethers suitable for use herein, a preferred macromer is poly(ethylene glycol). Poly(ethylene glycol) is preferred because of its solubility in aqueous solutions. Likewise, cross-linked networks of poly(ethylene glycol) swell in aqueous solutions. Non-polyether polymers with functional groups available for modification, such as poly(vinyl alcohol), can also be utilized as macromers. Preferred macromer concentrations range from about 5% w/w to about 50% w/w, about 10% w/w to about 40% w/w, about 15% w/w to about 30% w/w, or about 16% w/w to about 29% w/w of the polymerization solution. In one preferred embodiment, the macromer concentration is about 19% w/w, about 25% w/w or about 29% w/w of the polymerization solution.

In some embodiments, the macromer is shapeable. Shapeability describes the macromer's relative rigidity and its ability to hold a particular shape. For example, a shapeable macromer according to the present description can be formed using a device such as a mandrel and can hold the resulting shape for implantation.

The molecular weight of the macromer can dramatically change the resulting hydrogel's mechanical properties. Smaller molecular weights result in filaments with sufficient column strength to be pushed through microcatheters and catheters. Larger molecular weights result in filaments that can require more effort to be pushed through microcatheters and catheters. The macromers described herein have a molecular weight ranging from about 100 g/mole to about 100,000 g/mole or about 500 g/mole to about 50,000 g/mole. A preferred molecular weight ranges from about 5,000 g/mole to about 15,000 g/mole. In one embodiment, the molecular weight is about 10,000 g/mole.

Any functional groups associated with the macromers described can derivatized. The functional groups of the macromers can be derivatized to impart ethylenically unsaturated moieties allowing free radical polymerization of the hydrogel. Preferred functionalities for free radical polymerization include acrylates, methacrylates, acrylamides, vinyl groups, and derivatives thereof. Alternatively, other reactive chemistries can be employed to polymerize the hydrogel, for example, nucleophile/N-hydroxysuccinimde esters, nucleophile/halide, vinyl sulfone or maleimide. In one embodiment, a preferred functional group of the macromer is an acrylate.

Biostability (or non restorability) or biodegradation can be imparted to hydrogels described by altering the synthetic route to derivatize macromer functional groups. If biostability is desired, linkage stability in the physiological environment can be utilized. The preferred biostable linkage is an amide. The macromer hydroxyl group(s) is converted to an amino group followed by reaction with acryloyl chloride to form an acrylamide group. If biodegradation is desired, linkages susceptible to breakage in a physiological environment can be utilized. Preferred biodegradable linkages include esters, polyesters, and amino acid sequences degradable by enzymes. A preferred macromer is poly(ethylene glycol) diacrylamide with a molecular weight of about 10,000 g/mole.

Monomers sensitive to pH can be utilized in the hydrogels described herein thereby imparting environmental sensitivity to the hydrogel filaments. The main function of the pH sensitive monomer is to permit control over the hydrogel's rate of expansion. Such monomers must include functionality allowing incorporation into the resulting hydrogel during polymerization and ionizable moieties, for example, carboxylic acids or amines. Preferred concentrations of pH sensitive monomers in the polymerization solution range from about 1% to about 12.5%. Preferred pH sensitive monomers are acrylic acid, methacrylic acid, amino methacrylate, amino methacrylamide, and derivatives and salts thereof. In some embodiments, pH sensitive monomers are not utilized.

Generally, the controlled rate of expansion of the hydrogel filaments is imparted through the incorporation of ethylenically unsaturated monomers with ionizable functional groups, (e.g. acidic or basic groups). For example, if acrylic acid is incorporated into the cross-linked polymeric network the hydrogel can be introduced through a microcatheter filled with blood or saline at physiological pH. The hydrogel cannot and may not expand until the carboxylic acid groups deprotonate. Conversely, if a basic, amine containing monomer is incorporated into the cross-linked network, the hydrogel can be introduced through a microcatheter filled with blood or saline at physiological pH. The hydrogel cannot and will not fully expand until the amine groups are protonated.

In one embodiment, pH-sensitive monomers are incorporated into the polymer filaments to control the rate of expansion to permit delivery through microcatheters and catheters filled with physiological fluids. In one embodiment, ethylenically unsaturated carboxylic acids are incorporated into the polymer filaments. In another embodiment, salts of ethylenically unsaturated carboxylic acids are incorporated in to the polymer filaments and subsequently the polymer filaments are incubated in a low pH solution to protonate all the salts of the carboxylic acids. Expansion occurs in a physiological environment as the carboxylic acids deprotonate. In another embodiment, salts of ethylenically unsaturated amines are incorporated into the polymer filaments and subsequently the polymer filaments are incubated in a high pH solution to deprotonate the salts of the amines. Expansion occurs in a physiological environment as the amines protonate. In yet another environment, pH sensitive monomers are not incorporated into the polymer filaments.

Non-pH sensitive monomers can also be used to aid in polymerization of the hydrogel and impart specific mechanical properties to the resulting hydrogel. The non-pH sensitive monomers can be any molecule with a single functionality to incorporate into the resulting hydrogel and preferably a structure conducive to the desired mechanical property. The non-pH sensitive monomers can be, for example, hydrophobic thereby imparting column strength to the resulting hydrogel. Also or in addition, the non-pH sensitive hydrogel can have a bulky structure further imparting column strength to the resulting hydrogel. Internal hydrogen bonding within the non-pH sensitive monomer imparts increasing tensile strength. Preferred non-pH sensitive monomers are t-butyl acrylamide, 2-hydroxyethyl methacrylate, and derivatives thereof. Preferred concentrations of non-pH sensitive monomers range from about 0% to about 20% w/w, about 15% w/w, about 12% w/w or about 11% w/w of the polymerization solution.

In one embodiment, depending on the monomers chosen for a particular hydrogel, significant fluid uptake by the polymer filament occurs and a large increase in the volume of the polymer filaments occurs in a physiological environment. In another embodiment, monomers chosen allow only a small amount of fluid uptake by the polymer filament and only a small increase in the volume of the polymer filament occurs in a physiological environment. In yet another environment, monomers chosen prevent fluid uptake by the polymer filament and the volume of the polymer filaments remains unchanged in a physiological environment.

Cross-linker(s), when used in the described hydrogels, impart desired mechanical properties. The cross-linker can be any molecule with at least two functionalities to incorporate into the resulting hydrogel and preferably a structure conducive to the desired mechanical property. A preferred cross-linker is N,N-methylenebisacrylamide. Preferred concentrations of the cross-linker are less than about 1% w/w, less than about 0.8% w/w, less than about 0.5% w/w, or less than about 0.1% w/w of the polymerization solution. In one embodiment, the concentration of cross-linker is about 1% w/w.

In one embodiment, polymerization is imitated by azobisisobutyronitrile (AIBN) or a water soluble AIBN derivative. Other initiators useful according to the present description include N,N,N',N'-tetramethylethylenediamine, ammonium persulfate, benzoyl peroxides, 2,2'-azobis(2-methylpropionamidine)dihydrochloride, and combinations thereof, including azobisisobutyronitriles. The polymerization solution can be polymerized by reduction-oxidation, radiation, heat, or any other method known in the art. Radiation cross-linking of the polymerization solution can be achieved with ultraviolet light or visible light with suitable initiators or ionizing radiation (for example, electron beam or gamma ray) without initiators. Cross-linking can be achieved by application of heat, either by conventionally heating the solution using a heat source such as a heating well, or by application of infrared light to the polymerization solution.

When used in the polymerization solutions described herein, an initiator starts the polymerization of the polymerization solution components. An exemplary initiator includes 2,2'-azobis(2-methylpropionamidine)dihydrochloride. Preferred concentrations of the initiator are less than about 1% w/w or less than about 0.5% w/w of the polymerization solution.

Visualization agents can also be added to the hydrogels described herein since metallic support members are not used in conjunction with the presently described hydrogel filaments. Generally, in the art, metallic support members aid in the visualization of embolic devices. Here, this is not the case. The visualization agents impart visibility of the resulting hydrogel when imaged using a medically relevant imaging technique such as fluoroscopy, computed tomography, or magnetic resonance techniques.

Visualization of the hydrogel filaments under fluoroscopy can be imparted by the incorporation of solid particles of radiopaque materials such as barium, bismuth, tantalum, platinum, gold, and other heavy nuclei species into the hydrogel or by the incorporation of iodine molecules polymerized into the hydrogel structure. A preferred visualization agent for fluoroscopy is barium sulfate. Visualization of the hydrogel filaments under computed tomography imaging can be imparted by incorporation of solid particles of barium or bismuth. Metals visible under fluoroscopy generally result in beam hardening artifacts that preclude the usefulness of computed tomography imaging for medical purposes. A preferred visualization agent for computed tomography imaging is barium sulfate. Preferred concentrations of barium sulfate rendering the hydrogel filaments visible using fluoroscopic and computed tomography imaging range from about 30% w/w to about 60% w/w, about 35% w/w to about 50% w/w, or about 39% w/w to about 47% w/w of the polymerization solution.

Visualization of the hydrogel under magnetic resonance imaging can be imparted by the incorporation of solid particles of superparamagnetic iron oxide or gadolinium molecules polymerized into the hydrogel structure. A preferred visualization agent for magnetic resonance is superparamagnetic iron oxide with a particle size of 10 microns. Preferred concentrations of superparamagnetic iron oxide particles to render the hydrogel visible using magnetic resonance imaging range from about 0.01% w/w to about 1% w/w, about 0.05% w/w to about 0.5% w/w, or about 0.1% w/w to about 0.6% w/w of the polymerization solution.

In one example embodiment, a hydrogel filament can be formed of a difunctional, low molecular weight, ethylenically unsaturated, shapeable macromer, an ethylenically unsaturated monomer, a visualization element, a cross-linker and an initiator.

In another embodiment, a hydrogel filament includes about 25% w/w poly(ethylene glycol) 10,000 diacrylamide, about 11% w/w sodium acrylate, about 1% w/w N,N-methylenebisacrylamide, about 63% barium sulfate, and about <1% 2,2'-azobis(2-methylpropionaamidine)dihydrochloride.

In yet another embodiment, a hydrogel filament includes about 29% w/w poly(ethylene glycol) 10,000 diacrylamide, about 12% w/w sodium acrylate, about 1% w/w N,N-methylenebisacrylamide, about 58% barium sulfate, and about <1% 2,2'-azobis(2-methylpropionaamidine)dihydrochloride.

The hydrogel filaments have many characteristic properties one of which is bending resistance. The filaments generally have a dry bending resistance of about 20 mg to about 200 mg, about 20 mg to about 32 mg or about 100 mg to about 200 mg. In the wet state, the bending resistance lowers drastically to about 2 mg to about 50 mg, about 2 mg to about 5 mg, or about 25 mg to about 50 mg.

Another characteristic is average ultimate tensile strength of the filaments. The hydrogel filaments described herein have an average ultimate tensile strength of about 0.18 lbf to about 0.65 lbf, about 0.18 lbf to about 0.25 lbf, or about 0.52 lbf to about 0.65 lbf.

Methods of preparing hydrogels and/or hydrogel filaments is also described. The polymerization solution is prepared by dissolving the macromer, pH sensitive monomers, non-pH sensitive monomers, cross-linker, initiator, and soluble visualization agents in the solvent. After dissolution of these components, an insoluble visualization agent can be suspended in the polymerization solution. Mixing of the polymerization solution containing an insoluble visualization agent with a homogenizer aids in suspension of the insoluble visualization agent.

Figure 1:
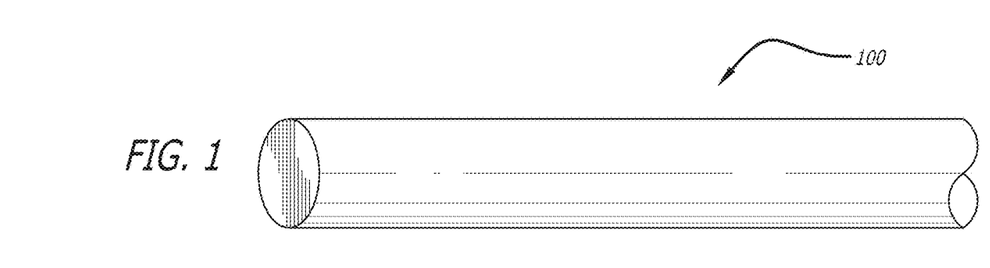
FIG. 1 illustrates a cylindrical hydrogel filament according to an embodiment of the present description.
Figure 2:
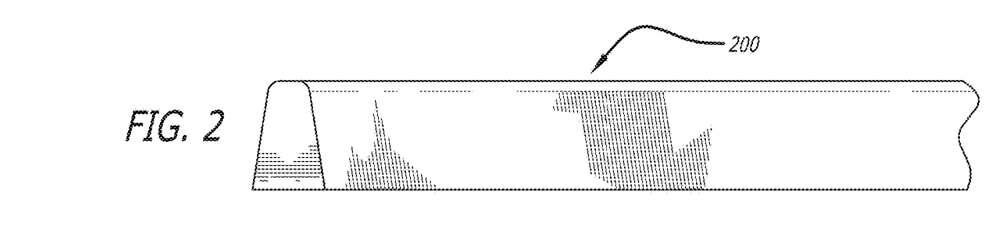
FIG. 2 illustrates a trapezoidal hydrogel filament according to an embodiment of the present description.
Figure 3:
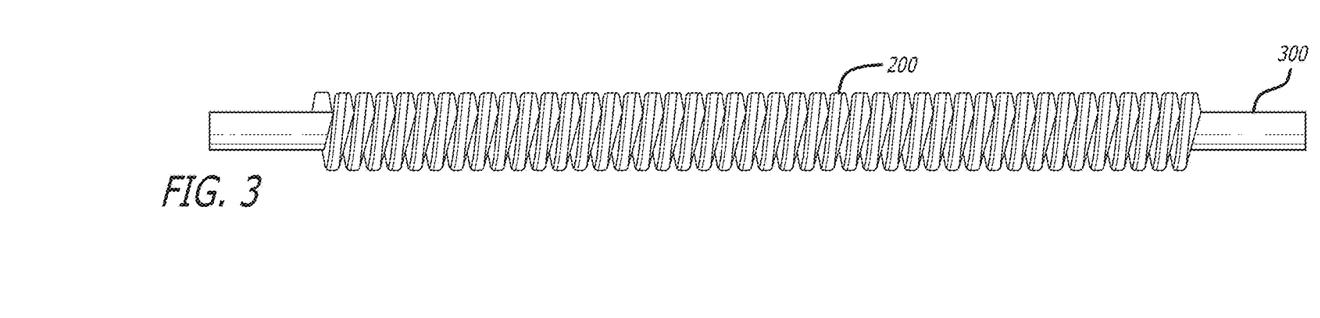
FIG. 3 illustrates the hydrogel filament of FIG. 2 wrapped around a mandrel to form a coil.

Then, the polymerization solution is injected into tubing with an inner diameter ranging from about 0.001 inches to about 0.075 inches and incubated for several hours in boiling water, for example, at 100° C., and subsequently overnight at 80° C. to complete the polymerization. The immersion in boiling water allows for rapid heat transfer from the water to the polymerization solution contained in the tubing. The selection of the tubing imparts microcatheter or catheter compatibility. For delivery through microcatheters, tubing diameters from about 0.006 inches to about 0.025 inches are preferred. For delivery through 4 and 5 Fr catheters, tubing diameters from about 0.026 inches to about 0.045 inches are preferred. In one embodiment, the tubing is made from HYTREL® (DuPont, Wilmington, Del.). The HYTREL® tubing can be dissolved in solvents, facilitating removal of the formed polymer hydrogel from the tubing. Exemplary hydrogel filament shapes are illustrated in FIGS. 1 and 2. FIG. 1 illustrates a cylindrical, circular or round filament 100 in a dried, straight state or configuration. Likewise, FIG. 2 illustrates trapezoidal filament 200 in a dried, straight state or configuration FIG. 3 illustrates one method of how a hydrogel coil is attained. If filament 200 is wrapped around a mandrel 300 prior to polymerization of the polymerization solution, the resulting polymer will maintain the shape of filament 200 around mandrel 300 or at least retain a memory of the shape. Using this technique, helical, tornado, and complex shapes can be imparted to the hydrogel filament. When the tubing is wrapped around a mandrel, the use of trapezoidal or oval tubing is preferred. After wrapping around the mandrel, the oval shape of the tubing is rounded and the resulting hydrogel filament has a round shape.

If HYTREL® tubing is utilized, the hydrogel filament can be recovered by incubating the tubing in a solution of 25% w/w phenol in chloroform followed by washing in chloroform and ethanol. After the hydrogel filament has been washed, it is dried, and a dried hydrogel filament is produced. The length of a dried filament can range from about 0.01 cm to about 1,000 cm, about 0.1 cm to about 500 cm, about 0.25 cm to about 250 cm, or about 0.5 cm to about 100 cm. The diameter of a filament can range from about 0.01 inches to about 0.1 inches, about 0.001 inches to about 0.01 inches, or about 0.006 inches to about 0.075 inches. In one embodiment the filament has a diameter less than about 0.05 inches, 0.04 inches, or 0.031 inches.

In some embodiments, the hydrogel filament can be incubated in a low pH or high pH solution to protonate or deprotonate the pH sensitive monomer incorporated into the hydrogel as necessary rendering it environmentally responsive.

Once the hydrogel has been synthesized and treated to produce the desired properties it is loaded into an introducer device that facilitates clinical use. The introducer device includes a tube appropriately sized for the implant and catheters being used. The tube's distal end is capped with a plug containing a small hole for de-airing the device. The tube's proximal end has a LUER-LOK® (Becton, Dickinson and Company, Franklin Lakes, N.J.) or similar fitting capped with a solid plug that prevents the device from migrating out of the introducer tubing. To prepare the device for clinical use, the proximal cap is removed and liquid (for example, saline) pushed through the introducer and distal cap thereby removing all air. The distal cap is then removed and the introducer tip seated in the catheter hub, optionally through a rotating hemostatic valve. After introduction of the device into the catheter with fluid pressure delivered via syringe the device may be advanced to the vascular site with fluid pressure delivered at the catheter hub, or optionally the hemostatic valve or optionally the back of the introducer.

Figure 4:
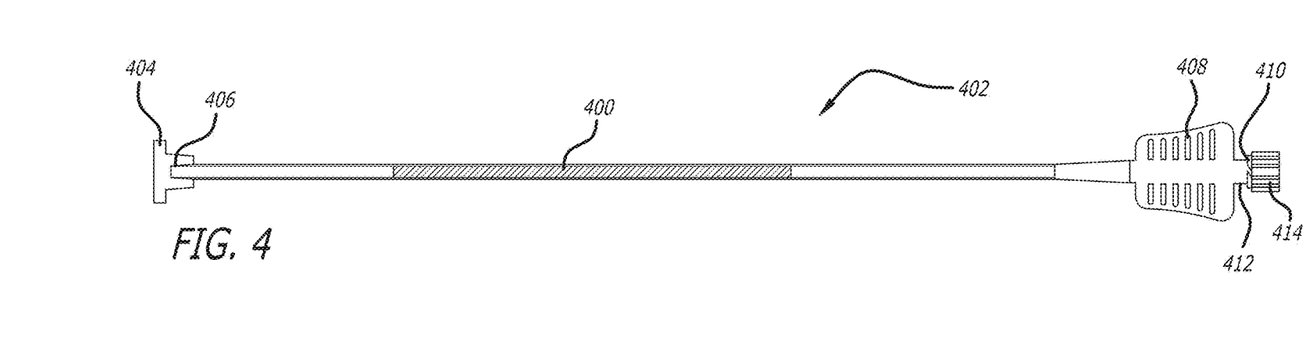
FIG. 4 illustrates a hydrogel filament according to an embodiment of the present description loaded into an introducer and capped for distribution.

As seen in FIG. 4, the dried hydrogel filament 400 is positioned within an introducer 402 prior to use in a treatment procedure. Preferably, both the introducer 402 and the dried hydrogel filament 400 can be sterilized and packaged for use at a later date.

When a user is ready to begin the procedure, a delivery system is used to deliver the hydrogel filament 400. The delivery system is generally a microcatheter. Introducer 402 can be connected to the delivery system after cap 404 has been removed from first end 406 of introducer 402. Hub 408 is used to grasp introducer 402 when connecting a liquid flush apparatus to connection point 410 a second end 412 of introducer 402. Connection point 410 can be plugged using cap 414.

Figure 5:
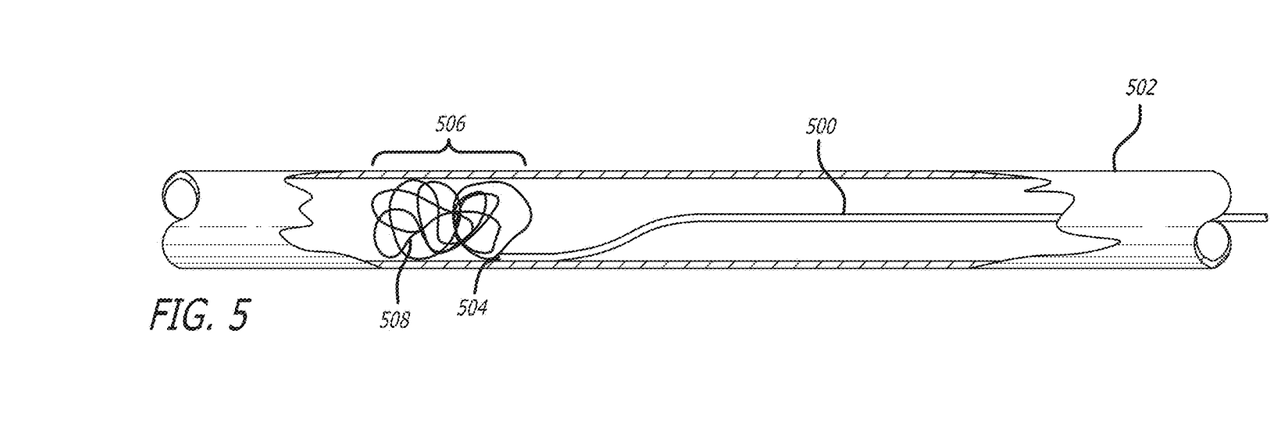
FIG. 5 illustrates a hydrogel filament according to an embodiment of the present description being injected via a catheter into a vessel.

Then, as illustrated in FIG. 5, a microcatheter's tubing 500 is advanced within a vessel 502 of a patient until distal end 504 is located at a target location 506 within vessel 502. Next, first end 406 of introducer 402 is connected to the delivery system and hub 408 is used to aid in connecting a syringe at connection point 410. Preferably the syringe contains saline or other physiological solution compatible for use within a patient.

The syringe delivers pressurized solution into introducer 402 so as to advance hydrogel filament 400 out of the introducer 402 and into the microcatheter. Once hydrogel filament 400 has completely entered the microcatheter, introducer 402 can be removed from the proximal end of the microcatheter and replaced with a syringe containing additional physiological solution.

When the user is ready to deliver hydrogel filament 400, the syringe is depressed, causing the physiological solution to pressurize within the microcatheter and push hydrogel filament 400 out of the distal end of the microcatheter and into the vessel 502 at target site 506, as seen in FIG. 5. As the hydrogel exits distal end 504 of the microcatheter, the hydrogel filament begins to naturally coil 508 if it had been formed around a mandrel. Preferably, hydrogel filament 400 then begins a controlled rate of expansion at target area 506.

The hydrogel filaments generally have characteristic deployment pressures when being flushed with a liquid. For example, de airing pressure range from about 5 psi to about 30 psi. On the other hand, introduction pressures range from about 50 psi to about 200 psi, about 50 psi to about 150 psi, or about 70 psi to about 200 psi. And delivery pressures range from about 60 psi to about 110 psi, about 60 psi to about 140 psi, or about 60 psi to about 110 psi.

Example 1

Preparation of Macromer

Four hundred and fifty grams of polyethylene glycol (PEG) 10,000 was dried by azeotropic distillation with 2400 mL of toluene. Then, 200 mL of dichloromethane, 15.6 mL of triethylamine was added with 10.4 mL of acryloyl chloride and stirred for 4 hr. The solution was filtered, the product precipitated in diethyl ether, and then collected by filtration. The resulting product was vacuum dried and then added to 3600 mL of 25% ammonia hydroxide and stirred closed for 4 days, then open for 3 days. The water was removed and the product dried by azeotropic distillation with toluene. To the resulting PEG diamine in toluene was added 15.6 mL of triethylamine and 10.9 mL of acryloyl chloride and the reaction was stirred for 4 hr. The resulting solution was filtered, precipitated in ether and the solvent removed yielding PEG 10,000 diacrylamide.

Example 2

Preparation of a Radiopaque Hydrogel Filament

To prepare a radiopaque hydrogel, 18 g of PEG 10,000 diacrylamide made according to Example 1, 0.25 g of 2,2'-Azobis(2-methylpropionamidine) dihydrochloride, 0.6 g of methylenebisacrylamide, and 7.5 g of sodium acrylate were dissolved in 25 g of water. Then, 41.08 g of solution was filtered and 38 g of barium sulfate was added. The resulting solution was sparged with argon for 10 minutes, then injected into 0.020 inch ID HYTREL tubing with a 3 cubic centimeter syringe. The tubing was heat sealed then polymerization initiated by leaving the sealed tube in boiling water for at least 1 hr. Polymerization was then continued by placing the tubing in an 80° C. oven overnight.

Example 3

Preparation of Hydrogel Filament Device

The polymerized polymer in tubing from Example 2 was placed in a solution of 20 wt % phenol in chloroform and this solution replaced once to remove the HYTREL tubing. The freed filament was then washed in chloroform three times and then dried in a vacuum oven. The filaments were then washed in water three times and then incubated in 1N HCl for 4 hours. The acid treated filaments were washed in isopropyl alcohol three times and dried in a vacuum oven.

Example 4

Bench Evaluation of Hydrogel Filament Device

The bending resistances of the unexpanded hydrogel samples were obtained using a Gurley 4171ET tubular stiffness tester with a 5 g counterweight attached to its measuring vane. The sample length was 1.25 inch and the resistance measured 0.25 inches from the free end. Polymer samples were tested dry and after 1 minute of hydration in 37° C. PBS.

System A is a hydrogel filament including 25% w/w poly(ethylene glycol) 10,000 diacrylamide, 11% w/w sodium acrylate, 1% w/w N,N-methylenebisacrylamide, 63% barium sulfate, and <1% 2,2'-azobis(2-methylpropionaamidine)dihydrochloride.

System B is a hydrogel filament including 29% w/w poly(ethylene glycol) 10,000 diacrylamide, 12% w/w sodium acrylate, 1% w/w N,N-methylenebisacrylamide, 58% barium sulfate, and <1% 2,2'-azobis(2-methylpropionaamidine)dihydrochloride.

| System | Sample Size | Dry Bending Resistance (mg) | Wet Bending Resistance (mg) |
|---|---|---|---|
| A | 10 | 27.417 ± 4.316 | 3.33 ± 1.047 |
| B | 10 | 146.52 ± 38.862 | 39.072 ± 10.211 |

The dry tensile strength of the polymer filaments was determined using an Instron test stand, a 5N load cell, a grip/clamp fixture and Bluehill software. Polymer filaments were inserted between the fixtures and the maximum load at breakage determined with the 5N load cell.

| System | Sample Size | Average Ultimate Tensile Strength (lbf) | Minimum (lbf) |
|---|---|---|---|
| A | 22 | 0.21 ± 0.03 | 0.131 |
| B | 22 | 0.58 ± 0.06 | 0.446 |

The expansion characteristics of the polymer filaments were determined using a video inspection station. First, the dry length and diameter of a polymer filament section was measured. Then, the polymer was exposed to 37° C. phosphate buffered saline (PBS) and diameter and length measured every 5 minutes. The PBS was replaced every 10 minutes to minimize the effects of PBS cooling on polymer expansion.

System A

| Sample Wind | Sample Size | Dry Average Diameter (in) | Dry Diameter Range (in) | 60 min Wet Average Diameter (in) | 60 min Wet Diameter range (in) |
|---|---|---|---|---|---|
| 2 mm | 11 | 0.0167 ± 0.0017 | 0.0150-0.0198 | 0.029 ± 0.0023 | 0.0266-0.0327 |
| 10 mm | 11 | 0.0155 ± 0.0007 | 0.0145-0.0166 | 0.0292 ± 0.0008 | 0.0281-0.0307 |

System B

| Sample Wind | Sample Size | Dry Average Diameter (in) | Dry Diameter Range (in) | 60 min Wet Average Diameter (in) | 60 min Wet Diameter range (in) |
|---|---|---|---|---|---|
| 4 mm | 11 | 0.0287 ± 0.0016 | 0.0263-0.0307 | 0.0515 ± 0.0028 | 0.0466-0.0553 |
| 15 mm | 11 | 0.0257 ± 0.0012 | 0.0240-0.0283 | 0.0493 ± 0.0014 | 0.0471-0.0508 |

The pressures required for preparing, introducing, and deploying the polymer filaments were determined in a silicone vascular model using a fluid pressure gauge connected to the syringe and introducer hub or catheter hub via a 3-way stopcock. Devices were de-aired, introduced into the catheter and deployed under saline drip, recording the maximum pressure for each step. Results are tabulated below.

System A

| Sample Size | De Airing Pressure (psi) | Introduction Pressure (psi) | Delivery Pressure (psi) |
|---|---|---|---|
| 22 | 20.82 ± 10.15 | 104.73 ± 51.53 | 99.14 ± 35.41 |

System B

| Sample Size | De Airing Pressure (psi) | Introduction Pressure (psi) | Delivery Pressure (psi) |
|---|---|---|---|
| 22 | 6.50 ± 1.87 | 128.55 ± 66.81 | 85.50 ± 27.61 |

Example 5

In Vitro Evaluation of Hydrogel Filament Device

Hydrogel filament devices were deployed in a silicone vascular model to test preparation, introduction, tracking and deployment characteristics using standard catheter techniques.

Example 6

In Vivo Evaluation of Hydrogel Filament Device

Hydrogel filaments loaded with barium were evaluated for in vivo performance in porcine arteries. Vascular sites were embolized with the hydrogel filaments and the animals sacrificed at either 7 or 90 days. During the procedures devices were scored in the following categories: Post embolization and pre-sacrifice, angiography was used to determine the occlusion of the embolization sites. Post sacrifice the embolization sites were harvested, imbedded in paraffin and/or methyl methacrylate and then sectioned to evaluate histologically.

Example 7

CT Evaluation of Hydrogel Filament Device

Experimental rabbit aneurysms were created in New Zealand white rabbits and filled with barium sulfate impregnated polymer filaments under fluoroscopic imaging. Post operation, the rabbits were imaged with a 10-multisectional helical CT machine (Brilliance 10, Philips Medical Systems, Best, Netherlands). FIG. 6 shows the results.

Figure 6A:
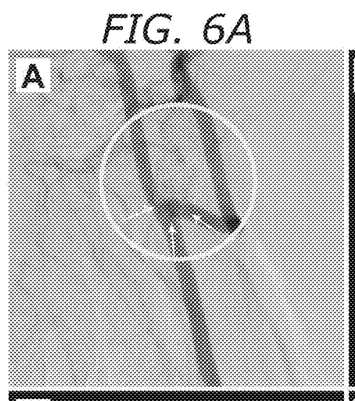
FIG. 6A illustrates post treatment DSA showing complete occlusion of the aneurysm (circle) and parent artery incursions (arrows).
Figure 6B:
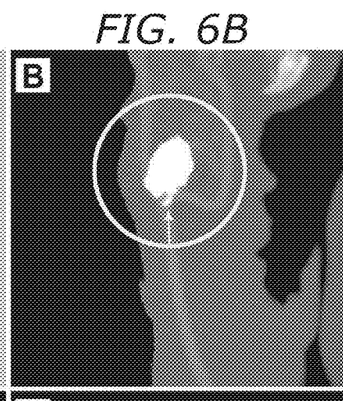
FIG. 6B illustrates a coronal image of a rabbit 13 weeks post embolization showing filaments in the aneurysm and parent artery (circle) with minor beam hardening artifacts.
Figure 6C:
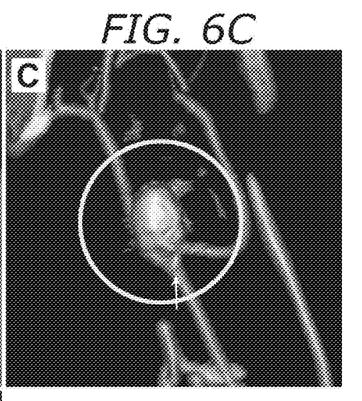
FIG. 6C illustrates a 3D CT reconstruction image of a rabbit 13 weeks post embolization showing filaments in the aneurysm and parent artery (circle) with minor beam hardening artifacts. The parent artery incursion was evident in both FIGS. 6B and 6C (arrows).
Figure 6D:
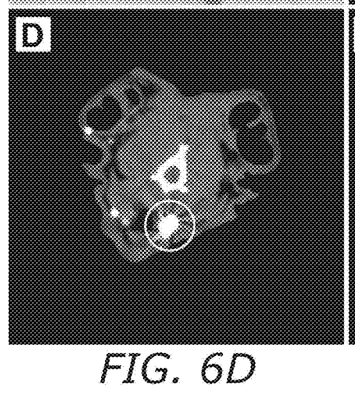
FIGS. 6D and 6E illustrate axial CT images showing hydrogel filaments in the parent artery (arrows) and the aneurysm sac (circle) with minor beam hardening artifacts.
Figure 6E:
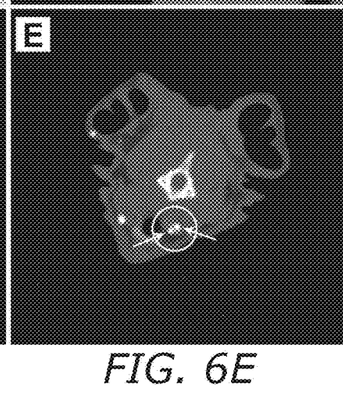

FIG. 6A is a vessel post treatment digital subtraction angiography showing complete occlusion of the aneurysm and parent artery incursions. FIGS. 6B and 6C are respectively a coronal and three dimensional reconstruction computer tomography images of a rabbit thirteen weeks post-embolization showing filaments in the aneurysm and parent artery with minor beam hardening artifacts. The parent artery incursion was evident in both the coronal and reconstructed images. FIGS. 6D and 6E are respectively axial computed tomography images showing hydrogel filaments in the parent artery and the aneurysm sac with minor beam hardening artifacts.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of forming a polymeric filament, the method comprising:
    polymerizing a solution to create a polymeric filament including about 25% w/w poly (ethylene glycol) 10,000 macromer, about 11% w/w of an ethylenically unsaturated monomer, and about 63% w/w barium sulfate,
    wherein the polymeric filament is configured to be loaded into an introducer configured to be connected to a catheter.

2. The method of claim 1, further comprising treating the polymeric filament in a non-physiological pH for a predetermined amount of time thereby creating an environmentally responsive filament.

3. The method of claim 2, wherein the non-physiological pH is acidic.

4. The method of claim 2, wherein the non-physiological pH is basic.

5. The method of claim 1, wherein the polymerizing includes polymerization in a tube.

6. The method of claim 1, wherein the at least one ethylenically unsaturated monomer is a pH sensitive monomer selected from acrylic acid, methacrylic acid, amino methacrylate, amino methacrylamide, or a combination thereof.

7. The method of claim 1, wherein the polymeric filament has a diameter of less than about 0.03 inches.

8. The method of claim 1, wherein the polymerization solution includes a multifunctional, ethylenically unsaturated cross-linker.

9. The method of claim 1, wherein the polymeric filament is configured to be flushed from the introducer into a catheter using a first pressurized liquid having a pressure of between about 50 psi and about 200 psi.

10. The method of claim 9, wherein the polymeric filament is configured to be flushed from the catheter using a second pressurized liquid having a pressure of between about 60 psi and about 140 psi.

11. A method of forming a hydrogel, the method comprising:
    polymerizing a solution to create a polymeric filament including about 29% w/w poly (ethylene glycol) 10,000 macromer, about 12% w/w of an ethylenically unsaturated monomer, and about 58% w/w barium sulfate,
    wherein the polymeric filament is configured to be loaded into an introducer configured to be connected to a catheter.

12. The method of claim 11, further comprising treating the polymeric filament in a non-physiological pH for a predetermined amount of time thereby creating an environmentally responsive filament.

13. The method of claim 12, wherein the non-physiological pH is acidic.

14. The method of claim 12, wherein the non-physiological pH is basic.

15. The method of claim 11, wherein the polymerizing includes polymerization in a tube.

16. The method of claim 11, wherein the at least one ethylenically unsaturated monomer is a pH sensitive monomer selected from acrylic acid, methacrylic acid, amino methacrylate, amino methacrylamide, or a combination thereof.

17. The method of claim 11, wherein the polymeric filament has a diameter of less than about 0.03 inches.

18. The method of claim 11, wherein the polymerization solution includes a multifunctional, ethylenically unsaturated cross-linker.

19. The method of claim 11, wherein the polymeric filament is configured to be flushed from the introducer into a catheter using a first pressurized liquid having a pressure of between about 50 psi and about 200 psi.

20. The method of claim 19, wherein the polymeric filament is configured to be flushed from the catheter using a second pressurized liquid having a pressure of between about 60 psi and about 140 psi.

* * * * *